(12) United States Patent
Elfstrom

(10) Patent No.: US 11,666,184 B2
(45) Date of Patent: Jun. 6, 2023

(54) DISPENSER FOR DISPENSING A HYGIENE PRODUCT AND ASSOCIATED METHOD OF OPERATING

(71) Applicant: Essity Hygiene and Health Aktiebolag, Gothenburg (SE)

(72) Inventor: Boris Allan Elfstrom, Philadelphia, PA (US)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 422 days.

(21) Appl. No.: 16/647,736

(22) PCT Filed: Sep. 20, 2017

(86) PCT No.: PCT/EP2017/073757
§ 371 (c)(1),
(2) Date: Mar. 16, 2020

(87) PCT Pub. No.: WO2019/057270
PCT Pub. Date: Mar. 28, 2019

(65) Prior Publication Data
US 2020/0229655 A1 Jul. 23, 2020

(51) Int. Cl.
*A47K 5/12* (2006.01)
*G01S 17/04* (2020.01)
(Continued)

(52) U.S. Cl.
CPC ............ *A47K 5/1217* (2013.01); *A47K 10/38* (2013.01); *G01S 17/04* (2020.01); *G01S 17/58* (2013.01);
(Continued)

(58) Field of Classification Search
CPC .............................. A47K 5/1217; A47K 10/38
See application file for complete search history.

(56) References Cited

U.S. PATENT DOCUMENTS 8,879,048 B2  11/2014 Mellot
9,624,655 B2   4/2017 Gregory et al.
(Continued)

FOREIGN PATENT DOCUMENTS

EP  3203356 A2   8/2017
EP  3248523 A2  11/2017
(Continued)

OTHER PUBLICATIONS

International Searching Authority, Search Report and Written Opinion issued in International Application No. PCT/EP2017/073757 dated Aug. 8, 2018 (19 pages).
(Continued)

*Primary Examiner* — Timothy R Waggoner
(74) *Attorney, Agent, or Firm* — Cantor Colburn LLP

(57) ABSTRACT

A dispenser is provided for dispensing a hygiene product. The dispenser includes a time-of-flight sensor for measuring a position of an object relative to the dispenser; and a controller configured to selectively operate at least one function of the dispenser based on the measured position of the object relative to the dispenser. A method of operating at least one function of a dispenser for dispensing a hygiene product is also provided. The method includes measuring with a time-of-flight sensor a position of an object relative to the dispenser; and using a controller to selectively operate the at least one function of the dispenser based on the measured position of the object relative to the dispenser.

15 Claims, 8 Drawing Sheets

(51) Int. Cl.
    *A47K 10/38*     (2006.01)
    *G01S 17/58*     (2006.01)
    *G01S 17/88*     (2006.01)
    *A61F 13/551*    (2006.01)
    *G07F 11/00*     (2006.01)
    *G07F 13/00*     (2006.01)

(52) U.S. Cl.
    CPC ........... *G01S 17/88* (2013.01); *A61F 13/5514* (2013.01); *G07F 11/00* (2013.01); *G07F 13/00* (2013.01)

(56) References Cited

U.S. PATENT DOCUMENTS

| | | | |
|---|---|---|---|
| 9,625,569 B2 | 4/2017 | Lange | |
| 2003/0102447 A1 | 6/2003 | Williams | |
| 2008/0116356 A1* | 5/2008 | Mok | H03K 17/943 250/208.1 |
| 2012/0085780 A1* | 4/2012 | Landauer | A47K 5/12 222/105 |
| 2013/0200097 A1* | 8/2013 | Yang | H05K 13/00 222/52 |
| 2015/0216370 A1 | 8/2015 | Lightner et al. | |
| 2015/0268342 A1 | 9/2015 | Iott et al. | |
| 2015/0338509 A1 | 11/2015 | Lange | |
| 2015/0355707 A1 | 12/2015 | Schindler et al. | |
| 2016/0273197 A1 | 9/2016 | Gregory et al. | |
| 2016/0309967 A1 | 10/2016 | Pelfrey et al. | |
| 2017/0051481 A1 | 2/2017 | Mercer | |
| 2017/0215655 A1* | 8/2017 | Ophardt | G06F 3/167 |
| 2017/0277272 A1* | 9/2017 | Nordin | H04B 10/502 |
| 2017/0319014 A1* | 11/2017 | Ophardt | B65F 1/14 |

FOREIGN PATENT DOCUMENTS

| | | |
|---|---|---|
| FR | 3026119 B1 | 12/2016 |
| WO | 2016154512 A1 | 9/2016 |

OTHER PUBLICATIONS

Australian Government IP Australia, Examination Report No. 2, Application No. 2017432648, dated Feb. 17, 2021 (6 pages).

Australian Government IP Australia, Examination Report issued in Australian Application No. 2017432648 dated Sep. 30, 2020 (6 pages).

Russian Federal Service for Intellectual Property, Official Action and Search Report issued in Russian Application No. 2020113683/28(023152) dated Oct. 9, 2020 with English Translations (17 pages).

* cited by examiner

DISPENSER FOR DISPENSING A HYGIENE PRODUCT AND ASSOCIATED METHOD OF OPERATING

CROSS-REFERENCE TO RELATED APPLICATION

This application is a national phase entry of, and claims priority to, International Application No. PCT/EP2017/073757, filed Sep. 20, 2017. The above-mentioned patent application is incorporated herein by reference in its entirety.

TECHNICAL FIELD

This application relates to dispensers, and more particularly, relates to dispensers for dispensing a hygiene product and which include a sensor.

BACKGROUND

Dispensers are known that operate a dispensing function based on a location of an object—such as a user or part of the user's body. Dispensers of that type may have a sensor that emits some form of energy (e.g., microwave, infrared), and monitor for the detection of a reflection above a predetermined threshold. Reflection of the emitted energy above the predetermined threshold may be an indication that the object is in close proximity to the sensor, and upon such detection, the dispenser operates the dispensing function of the dispenser.

Dispensers of the type described above rely to a great extent on the reflectivity of the object, as well as on external characteristics of the room in which the dispenser and object are located. In order to avoid inadvertent operation of the dispensing function when there is no object in the vicinity of the dispenser, the threshold is set to a relatively large value. A drawback of doing so, however, is that the object has to be very close to the sensor of the dispenser in order for the dispensing function to be triggered.

It would be desirable, accordingly, to provide dispensers that may be reliably operated when objects are located at relatively large distances from the dispenser. It is also desirable to develop methods of operating dispensers that address these and other drawbacks discussed above.

SUMMARY

To address the problems with conventional dispenser designs and methods, according to some embodiments of the present invention, a dispenser is provided for dispensing a hygiene product, including: a time-of-flight sensor for measuring a position of an object relative to the dispenser; and a controller configured to selectively operate at least one function of the dispenser based on the measured position of the object relative to the dispenser.

Throughout this disclosure, the term "hygiene product" refers to a dispensable product that is used for hygienic purposes. For example, hygiene products include napkins (woven or nonwoven in the form of sheets or rolls), liquids (soap, disinfectant), and feminine hygiene articles.

Throughout this disclosure, the term "time-of-flight sensor" refers to any sensor that is configured to emit a certain form of energy and to measure the time it takes for the emitted energy to be reflected back to the sensor. The distance between the sensor and an object causing the reflection may be calculated by the sensor based on the measured time and the predetermined speed of travel of the emitted energy.

For example, the time-of-flight sensor may be any of the sensors described in U.S. Pat. No. 8,879,048, the entirety of which is incorporated herein by reference.

In one embodiment, the time-of-flight sensor is configured to emit pulses of light and to detect the reflection of the reflected pulses.

In one embodiment, the light is infrared light. The time-of-flight sensor comprises an infrared emitting diode configured to emit the pulses of infrared light and an infrared detector to detect the reflection of the reflected infrared pulses.

Each time-of-flight sensor may have a detection region which is a region in which the time-of-flight sensor may be able to measure the distance of an object.

In sensors of the type described above, the emitted energy may be in the form of light or sound, for example. The energy may be emitted in pulses at a sample rate.

The time-of-flight sensor may be configured to determine the position of the object (i.e., causing the reflection) in one dimension, two dimensions or three dimensions. The position may be represented by a vector (i.e., a one-dimensional vector, a two-dimensional vector or a three-dimensional vector).

Throughout this disclosure, the term "time-of-flight sensor" is intended to refer to one, two, or more time-of-flight sensors. In certain embodiments, a combination of two or more time-of-flight sensors may be used to determine the position of the object in two or three dimensions. In other embodiments, one time-of-flight sensor emits energy in multiple directions so as to determine the position of the object in two or three dimensions.

The term "object" in the context of this disclosure includes a user or a part of a user's body, such as a hand.

A function of the dispenser may be any process that the dispenser may carry out. An operation of the function is the triggering of this process of the dispenser.

As the sensor is a time-of-flight sensor, the sensor is minimally influenced by the reflectivity of the object or the surrounding environment. Accordingly, the controller may be set to operate at least one function of the dispenser when there is a greater distance between the object and the sensor, without risk of false (i.e., unintended) operation of the function.

Hence, with such a configuration, it is possible to provide a dispenser that may be operated at a larger distance while minimizing the risk of false operation.

In one embodiment, the time-of-flight sensor is configured to operate at a first sample rate when the measured position is in a first zone and at a second sample rate when the measured position is in a second zone, the first sample rate being higher than the second sample rate.

Throughout this disclosure, the term "sample rate" refers to the rate at which the time-of-flight sensor emits pulses of energy, which corresponds (at least in part) to the rate at which measurements of the reflection time are taken. Accordingly, a higher sample rate may result in a higher rate of determination of the distance to the object.

The term "zone" defines a spatial region relative to the dispenser delimited by a range in one of the three dimensions, two of the three dimensions or three of the three dimensions. A point within a zone may be represented by a vector (i.e., a one-dimensional vector, a two-dimensional vector or a three-dimensional vector).

As the power consumption of the sensor increases with an increase in the sample rate, the power consumption of the sensor may be decreased in certain zones which are not critical to the operation of the dispenser, without compromising the overall performance of the dispenser.

Hence, with such a configuration, the power consumption of the sensor may be decreased without compromising the overall performance of the dispenser.

In one embodiment, the time-of-flight sensor is configured to switch from operating at a second sample rate to operating at a first sample rate when the position of the object is first measured to be in the first zone, the first sample rate being higher than the second sample rate. In one embodiment, the time-of-flight sensor is configured to remain operating at the first sample rate until a predetermined condition is met. In one embodiment, the predetermined condition is an elapsed amount of time from when the object is first measured to be in the first zone. In one embodiment, the predetermined condition is a measurement of the object outside the first zone. In one embodiment, the predetermined condition is a measurement of the object in the second zone. In one embodiment, once the predetermined condition is met, the time-of-flight sensor is configured to switch from operating at the first sample rate to operating at the second sample rate.

In another embodiment, the controller is configured to operate a first function of the at least one function when the measured position is in a first zone, and wherein the controller is configured to operate a second function of the at least one function when the measured position is in a second zone.

With such a configuration, it is possible to provide a dispenser that allows for convenient operation of two different functions of the dispenser.

In a further embodiment, the first function is a dispensing function.

In one embodiment, the second function is a power-up function or a display function.

A dispensing function of the dispenser dispenses an amount of the hygiene product from the dispenser such that this amount of the hygiene product is delivered to the user or is ready for the user to take from the dispenser.

In a non-limiting example, the dispensing function may include actuation of a dispensing element of the dispenser such that a predetermined amount of the hygiene product is delivered to an opening of the dispenser.

A power-up function of the dispenser may turn on an electrical element of the dispenser. For example, the power-up function may transition an electrical element from an "off" state to an "on" state. In another example, the power-up function may transition an electrical element from a "sleep" state to an "on" state.

A display function of the dispenser may display information to the user in a specified manner. For example, a display function may display information on a LCD display of the dispenser or turn on certain LEDs of the dispenser.

In one embodiment, the first function is a dispensing function and the second function is a power-up function.

In another embodiment, the first function is a dispensing function and the second function is a display function.

In other embodiments, the first function is a dispensing function and the second function is a communication function, a sound function, or a settings function.

A settings function of the dispenser may alter one or more settings of the dispenser.

In one embodiment, the first function is a dispensing function that dispenses a first amount of the hygiene product and the second function is a dispensing function that dispenses a second amount of the hygiene product.

In another embodiment, the first function is a display function and the second function is a dispensing function, a power-up function, a communication function, a sound function, or a settings function.

In a further embodiment, the first function is a display function that displays a first piece of information and the second function is a display function that displays a second piece of information.

In yet another embodiment, the first zone is closer to the dispenser than the second zone.

In one embodiment, a first zone is closer to the dispenser than a second zone if the average magnitude of the vectors representing the points within the first zone is less than the average magnitude of the vectors representing the points within the second zone.

In another embodiment, the entirety of the first zone is closer to the dispenser than the entirety of the second zone.

In yet another embodiment, the entirety of the first zone may be closer to the dispenser than the entirety of the second zone if the magnitude of each of the vectors representing the points within the first zone is less than the magnitude of each of the vectors representing points within the second zone.

If the object is in the second zone, the rate of determination of the distance from the dispenser to the object may not be a critical factor as the user may not be immediately looking to interact with a function of the dispenser due to the relatively large separation between that object and the dispenser.

Hence, with such configurations, the power consumption of the sensor may be decreased without compromising the performance of the dispenser.

As used herein, "R" refers to a distance from a point on a face of the dispenser along a specific direction away from the dispenser. In one embodiment, the face of the dispenser includes a dispensing opening, and, optionally, wherein the point on the face of the dispenser (i.e., from which "R" is measured) is in the dispensing opening. In a specific embodiment, the face of the dispenser is configured to face the user. The direction associated with "R" may define an acute angle with the face of the dispenser, with that acute angle being between about 45° and about 90°. In a specific embodiment, that angle may be about 90° such that the direction is substantially perpendicular to the face of the dispenser.

In one embodiment, 0 cm<R<5 cm for the first zone, and, optionally, R≥5 cm for the second zone, and, further optionally, 5 cm≤R<500 cm for the second zone.

In one embodiment, the first zone extends from R=0 cm to R=5 cm, and, optionally, the second zone extends from R=5 cm, and, further optionally, the second zone extends from R=5 cm to R=500 cm.

In one embodiment, 0 cm<R<10 cm for the first zone, and, optionally, R≥10 cm for the second zone, and, further optionally, 10 cm≤R<500 cm for the second zone.

In one embodiment, the first zone extends from R=0 cm to R=10 cm, and, optionally, the second zone extends from R=10 cm, and, further optionally, the second zone extends from R=10 cm to R=500 cm.

In one embodiment, $\alpha$ defines an angle between a face of the dispenser and a line connecting a point on the face of the dispenser to a location. In one embodiment, $\alpha$ defines a horizontal angle.

In another embodiment, $\alpha$ defines a vertical angle. In one embodiment, $0° < \alpha < 60°$ for the first zone, and, optionally, α≥60° for the second zone, and, further optionally, 60°≤α<120° for the second zone.

In a further embodiment, the first zone extends from α=0° to α=60°, and, optionally, the second zone extends from α=60°, and, further optionally, the second zone extends from α=60° to α=120°.

In one embodiment, the time-of-flight sensor is configured to operate at a first sample rate when the measured position is in the first zone and at a second sample rate when the measured position is in the second zone, the first sample rate being higher than the second sample rate.

In another embodiment, the time-of-flight sensor is configured to switch from operating at a second sample rate to operating at a first sample rate when the position of the object is first measured to be in the first zone, the first sample rate being higher than the second sample rate. In one embodiment, the time-of-flight sensor is configured to remain operating at the first sample rate until a predetermined condition is met. In one embodiment, the predetermined condition is an elapsed amount of time from when the object is first measured to be in the first zone. In one embodiment, the predetermined condition is a measurement of the object outside the first zone. In one embodiment, the predetermined condition is a measurement of the object in the second zone. In one embodiment, once the predetermined condition is met, the time-of-flight sensor is configured to switch from operating at the first sample rate to operating at the second sample rate.

In yet another embodiment, the controller is configured to calculate a velocity of the object relative to the dispenser based on measured positions of the object, with the controller being configured to operate a first function of the at least one function if the velocity is within a first predetermined range of velocities.

The velocity of the object may be determined by calculating the change in the position of the object between two determined positions of the object, and dividing the change in the position by the time elapsed between the two determined positions.

The velocity may be represented by a vector (i.e., a one-dimensional vector, a two-dimensional vector or a three-dimensional vector).

A velocity is within a predetermined range of velocities if all components (one, two, or three) of the velocity fall within respective predetermined ranges for those velocity components.

A predetermined range of a velocity component may be defined as negative infinity to positive infinity, if such velocity component is not intended to be limited in any way.

Operating a function based on a velocity of an object may be desirable in order to permit intuitive operation of the dispenser.

Hence, with such a configuration, a function of the dispenser may be intuitively operated by the user.

In one embodiment, the first function is a dispensing function that dispenses a first, predetermined amount of hygiene product.

Without intending to be limiting, "amount" of the hygiene product may refer to a number of sheet products, a length of the product, a volume of the product (particularly liquid product) or a weight of the product.

With such a configuration, a dispensing function of the dispenser may be conveniently operated by the user.

In one embodiment, the controller is configured to operate a second function of the at least one function if the velocity is within a second predetermined range of velocities, with the second function being a dispensing function that dispenses a second amount of hygiene product.

The first amount and the second amount are different.

With such a configuration, different amounts of the hygiene product may be dispensed in a convenient manner by the user.

In one embodiment, the magnitude of at least some of the velocities of the first predetermined range is smaller than the magnitude of at least some of the velocities of the second predetermined range, and the first amount to be dispensed is smaller than the second amount.

The magnitude of the velocity of the object refers to the speed associated with movement of the object, irrespective of the direction of movement of such object.

In one embodiment, the magnitudes of all of the velocities within the first predetermined range are smaller than the magnitudes of all of the velocities within the second predetermined range, and the first amount to be dispensed is smaller than the second amount.

With such a configuration, different amounts of the hygiene product may be dispensed in a convenient, intuitive manner by the user.

In one embodiment, the controller is configured to calculate the speed of the object relative to the dispenser based on measured positions of the object, with the controller being configured to operate a first function of the at least one function if the speed is within a first predetermined range.

In another embodiment, the first function is a dispensing function that dispenses a first amount of hygiene product.

In a further embodiment, the controller is configured to operate a second function of the at least one function if the speed is within a second predetermined range, with the second function being a dispensing function that dispenses a second amount of hygiene product.

In one embodiment, the first predetermined range is smaller than the second predetermined range, and the first amount is smaller than the second amount.

In yet another embodiment, the first function is a display function that displays a first piece of information.

A piece of information may refer to information relating to operation or a characteristic of the dispenser.

In one embodiment, the piece of information is in the form of an indication of whether or not the dispenser is operational and/or associated with the amount of hygiene product remaining in the dispenser.

In another embodiment, the controller is configured to operate a second function of the at least one function if the measured velocity is within a second predetermined range of velocities, with the second function being a display function that displays a second piece of information.

The first piece of information and the second piece of information are different.

With such a configuration, different pieces of information may be presented to the user in a convenient manner.

In one embodiment, the controller is configured to operate a function of the dispenser only if the velocity of the object is in a prespecified direction, for example toward the dispenser.

A velocity is toward the dispenser if the vector associated with that velocity is directed toward the dispenser.

With such a configuration, unintended operation of a function of the dispenser may be avoided.

In one embodiment, one of the at least one function of the dispenser is a communication function in which the dispenser communicates with an external entity.

With such a configuration, communication of the dispenser may be triggered in a convenient manner.

In one embodiment, the controller is configured to determine a movement of the object relative to the dispenser based on measured positions of the object, and configured to operate a function of the at least one function of the dispenser if the determined movement is a predetermined movement. In one embodiment, the predetermined movement is a sideways movement relative to the dispenser. In one embodiment, the predetermined movement is a movement towards or away from the dispenser. In one embodiment, the predetermined movement is a sideways movement relative to the dispenser followed by a movement towards or away from the dispenser. In one embodiment, the predetermined movement is a movement towards or away from the dispenser followed by a sideways movement relative to the dispenser. In one embodiment, the predetermined movement is a first sideways movement relative to the dispenser followed by a second sideways movement relative to the dispenser.

In another embodiment, the function of the at least one function of the dispenser is a display function that displays a status of the dispenser, and, optionally, where the status is a product level, battery level or the like.

In yet another embodiment, the controller is configured to determine a movement of the object relative to the dispenser based on measured positions of the object, to operate a first function of the at least one function of the dispenser if the determined movement is a first predetermined movement, and to operate a second function of the at least one function of the dispenser if the determined movement is a second predetermined movement.

In one embodiment, the first function is a display function that displays a first status of the dispenser, and the second function is a display function that displays a second status of the dispenser. The first status and/or the second status may be a product level, battery level or the like.

In a further embodiment, the time-of-flight sensor comprises a first time-of-flight sensor and a second time-of-flight sensor. The controller is configured to determine a first movement of the determined movement based on measured positions of the object measured by the first time-of-flight sensor and a second movement of the determined movement based on measured positions of the object measured by the second time-of-flight sensor. Optionally, the first time-of-flight sensor and the second time-of-flight sensor are spaced apart from each other. In certain embodiments, the first time-of-flight sensor and the second time-of-flight sensor are spaced apart from each other in a horizontal or vertical direction.

In one embodiment, the controller is configured to operate a first function of the at least one function when the measured position of an object is in a first zone, configured to operate a second function of the at least one function when the measured position is in a second zone, and/or, configured to operate a third function of the at least one function when the measured position is in a third zone.

The first function may be a dispensing function that dispenses a first amount of hygiene product, a display function that displays a first piece of information, a power-up function that powers-up a first electrical element, a first communication function, a sound function that emits a first sound, and/or a first settings function.

The second function may be a dispensing function that dispenses a second amount of hygiene product, a display function that displays a second piece of information, a power-up function that powers-up a second electrical element, a second communication function, a sound function that emits a second sound, and/or a second settings function.

The third function may be a dispensing function that dispenses a third amount of hygiene product, a display function that displays a third piece of information, a power-up function that powers-up a third electrical element, a third communication function, a sound function that emits a third sound, and/or a third settings function.

The first zone may be closer to the dispenser relative to the location of the second zone. Additionally or alternatively, the second zone may be closer to the dispenser relative to the location of the third zone.

The entirety of the first zone may be closer to the dispenser than is the entirety of the second zone. Additionally or alternatively, the entirety of the second zone may be closer to the dispenser than is the entirety of the third zone.

In one embodiment, R defines a distance from a point on a face of the dispenser along a direction away from the dispenser. In one embodiment, the face of the dispenser has a dispensing opening and, optionally, the point on the face of the dispenser is located in the dispensing opening. In one embodiment, the face of the dispenser may be configured to face the user. In some embodiments, the direction associated with R may define an acute angle with the face of the dispenser, and lie, for example, between about 45° and about 90°. In one embodiment, the angle between the direction associated with R and the face of the dispenser is about 90° i.e., the direction is perpendicular to the face of the dispenser.

In another embodiment, $0 \text{ cm} < R < 5 \text{ cm}$ for the first zone, and, optionally, $R \geq 5 \text{ cm}$ for the second zone, and, further optionally, $5 \text{ cm} \leq R < 500 \text{ cm}$ for the second zone, and, yet further optionally, $500 \text{ cm} \leq R$ for the third zone, and, yet further optionally, $500 \text{ cm} \leq R \leq 1000 \text{ cm}$ for the third zone.

In yet another embodiment, the first zone extends from $R=0$ cm to $R=5$ cm, and, optionally, the second zone extends from $R=5$ cm, and, further optionally, the second zone extends from $R=5$ cm to $R=500$ cm, and, yet further optionally, the third zone extends from $R=500$ cm, and yet further optionally, the third zone extends from $R=500$ cm to $R=1000$ cm.

In a further embodiment, $0 \text{ cm} < R < 10 \text{ cm}$ for the first zone, and, optionally, $R \geq 10 \text{ cm}$ for the second zone, and, further optionally, $10 \text{ cm} \leq R < 500 \text{ cm}$ for the second zone, and, yet further optionally, $500 \text{ cm} \leq R$ for the third zone, and, yet further optionally, $500 \text{ cm} \leq R \leq 1000 \text{ cm}$ for the third zone.

In one embodiment, the first zone extends from $R=0$ cm to $R=10$ cm, and, optionally, the second zone extends from $R=10$ cm, and, further optionally, the second zone extends from $R=10$ cm to $R=500$ cm, and, yet further optionally, the third zone extends from $R=500$ cm, and yet further optionally, the third zone extends from $R=500$ cm to $R=1000$ cm.

In another embodiment, $i \text{ cm} < R < j \text{ cm}$ for the first zone, and, optionally, $R \geq j \text{ cm}$ for the second zone, and, further optionally, $j \text{ cm} \leq R < k \text{ cm}$ for the second zone, and, yet further optionally, $k \text{ cm} \leq R$ for the third zone, and, yet further optionally, $k \text{ cm} \leq R \leq l \text{ cm}$ for the third zone.

In a further embodiment, the first zone extends from $R=i$ cm to $R=j$ cm, and, optionally, the second zone extends from $R=j$ cm, and, further optionally, the second zone extends from $R=j$ cm to $R=k$ cm, and, yet further optionally, the third zone extends from $R=k$ cm, and yet further optionally, the third zone extends from $R=k$ cm to $R=l$ cm.

In one embodiment the value of i may be such that $0 \text{ cm} \leq i \leq 5 \text{ cm}$, specifically such that $0 \text{ cm} \leq i \leq 2.5 \text{ cm}$, more specifically such that $0 \text{ cm} \leq i \leq 1 \text{ cm}$.

In another embodiment the value of j may be such that 5 cm≤j≤15 cm, specifically such that 5 cm≤j≤10 cm, more specifically such that 6.5 cm≤j≤8.5 cm.

In yet another embodiment the value of k may be such that 200 cm≤k≤700 cm, specifically such that 300 cm≤k≤600 cm, more specifically such that 450 cm≤k≤550 cm.

In one embodiment the value of l may be such that 500 cm≤l≤1500 cm, specifically such that 800 cm≤l≤1200 cm, more specifically such that 950 cm≤l≤1050 cm.

In another embodiment, i=0 cm, 0.1 cm, 0.2 cm, 0.3 cm, 0.4 cm, 0.5 cm, 0.6 cm, 0.7 cm, 0.8 cm, 0.9 cm, 1 cm, 1.5 cm, 2 cm, 2.5 cm, 3 cm, 3.5 cm, 4 cm, 4.5 cm, 5 cm, 10 cm, 15 cm, 20 cm, 25 cm, 30 cm, 35 cm, 40 cm, 45 cm, 50 cm, 55 cm or 60 cm.

In yet another embodiment, j=0.1 cm, 0.2 cm, 0.3 cm, 0.4 cm, 0.5 cm, 0.6 cm, 0.7 cm, 0.8 cm, 0.9 cm, 1 cm, 1.5 cm, 2 cm, 2.5 cm, 3 cm, 3.5 cm, 4 cm, 4.5 cm, 5 cm, 10 cm, 15 cm, 20 cm, 25 cm, 30 cm, 35 cm, 40 cm, 45 cm, 50 cm, 55 cm, 60 cm, 65 cm, 70 cm, 75 cm, 80 cm, 85 cm, 90 cm, 95 cm or 100 cm.

In a further embodiment, k=5 cm, 10 cm, 15 cm, 20 cm, 25 cm, 30 cm, 35 cm, 405 cm, 45 cm, 50 cm, 55 cm, 60 cm, 65 cm, 70 cm, 75 cm, 80 cm, 85 cm, 90 cm, 95 cm, 100 cm, 150 cm, 200 cm, 250 cm, 300 cm, 350 cm, 400 cm, 450 cm, 500 cm, 550 cm, 600 cm, 650 cm, 700 cm, 750 cm, 800 cm, 850 cm, 900 cm, 950 cm or 1000 cm.

In one embodiment, l=100 cm, 150 cm, 200 cm, 250 cm, 300 cm, 350 cm, 400 cm, 450 cm, 500 cm, 550 cm, 600 cm, 700 cm, 750 cm, 800 cm, 850 cm, 900 cm, 950 cm, 1000 cm, 1050 cm, 1100 cm, 1150 cm, 1200 cm, 1250 cm, 1300 cm, 1350 cm, 1400 cm, 1450 cm or 1500 cm.

The symbol a represents an angle defined between a face of the dispenser and a line connecting a point on the face of the dispenser to a location. In one embodiment, α may be a horizontal angle. In another embodiment, α may be a vertical angle.

In one embodiment, 0°<α<60° for the first zone, and, optionally, α≥60° for the second zone, and, further optionally, 60°≤α<120° for the second zone, and, yet further optionally, 120°≤α for the third zone, and, yet further optionally, 120°≤α≤180° for the third zone.

In another embodiment, the first zone extends from α=0° to α=600, and, optionally, the second zone extends from α=60°, and, further optionally, the second zone extends from α=60° to α=120°, and, yet further optionally, the third zone extends from α=120°, and, yet further optionally, the third zone extends from α=120° to α=180°.

In a further embodiment, 0°<α<90° for the first zone, and, optionally, α≥90° for the second zone, and, further optionally, 90°≤α<180° for the second zone.

In one embodiment, the first zone extends from α=0° to α=90°, and, optionally, the second zone extends from α=90°, and, further optionally, the second zone extends from α=90° to α=180°.

In another embodiment, a°<α<b° for the first zone, and, optionally, α≥b° for the second zone, and, further optionally, b°≤α<c° for the second zone, and, yet further optionally, c°≤α for the third zone, and, yet further optionally, c°≤α≤d° for the third zone.

In yet another embodiment, the first zone extends from α=a° to α=b°, and, optionally, the second zone extends from α=b°, and, further optionally, the second zone extends from α=b° to α=c°, and, yet further optionally, the third zone extends from α=c°, and yet further optionally, the third zone extends from α=c° to α=d°.

In a further embodiment, 0°≤α≤5°, specifically 0°≤α≤2.5°, and more specifically 0°≤α≤1°.

In one embodiment, 40°≤b≤80°, specifically 50°≤b≤70°, and more specifically 55°≤b≤65°. In another embodiment, 70°≤b≤110°, specifically 80°≤b≤100°, and more specifically 85°≤b≤95°.

In another embodiment, 100°≤c≤140°, specifically 110°≤c≤130°, and more specifically 115°≤c≤125°. In another embodiment, 160°≤b≤200°, specifically 170°≤b≤190°, and more specifically 175°≤b≤185°.

In yet another embodiment, 160°≤d≤200°, specifically 170°≤d≤190°, and more specifically 175°≤d≤185°.

In a further embodiment, a=0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175° or 180°.

In one embodiment, b=0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175° or 180°.

In another embodiment, c=0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175° or 180°.

In yet another embodiment, d=0°, 5°, 10°, 15°, 20°, 25°, 30°, 35°, 40°, 45°, 50°, 55θ, 60°, 65θ, 70°, 75°, 80°, 85θ, 90°, 95°, 100°, 105θ, 110°, 115θ, 120°, 125°, 130°, 135θ, 140°, 145θ, 150°, 155θ, 160°, 165θ, 170°, 175° or 180°.

In a further embodiment, 90°−α$_1$/2≤α≤90°+α$_1$/2 for the first zone. In one embodiment, the first zone extends from α=90°−α$_1$/2 to α=90°+α$_1$/2.

In one embodiment, α$_1$=10°, 20°, 30°, 40°, 50°, 60°, 70°, 80°, 90°, 100°, 110°, 120°, 130°, 140°, 150°, 160°, 170° or 180°.

In another embodiment, 10°≤α$_1$≤50°, specifically 20°≤α$_1$≤40°, and more specifically 25°≤α$_1$≤35°.

In yet another embodiment, 90°−α$_2$/2≤α≤90°−α$_1$/2 and 90°+α$_1$/2≤α≤90°+α$_2$/2, for the second zone. In one embodiment, the second zone extends from α=90°−α$_2$/2 to α=90°−α$_1$/2, and from α=90°+α$_1$/2 to α=90°+α$_2$/2.

In a further embodiment, α$_2$=10°, 20°, 30°, 40°, 50°, 60°, 70°, 80°, 90°, 100°, 110°, 120°, 130°, 140°, 150°, 160°, 170° or 180°.

In one embodiment, 30°≤α$_2$≤110°, specifically 50°≤α$_1$≤90°, and more specifically 60°≤α$_1$≤80°.

In another embodiment, 90°−α$_3$/2≤α≤90°−α$_2$/2 and 90°+α$_2$/2≤α≤90°+α$_3$/2, for the third zone. In one embodiment, the third zone extends from α=90°−α$_3$/2 to α=90°−α$_2$/2, and from α=90°+α$_2$/2 to α=90°+α$_3$/2.

In yet another embodiment, α$_3$=10°, 20°, 30°, 40°, 50°, 60°, 70°, 80°, 90°, 100°, 110°, 120°, 130°, 140°, 150°, 160°, 170° or 180°.

In a further embodiment, 50°≤$_3$≤130°, specifically 70°≤$_3$≤120°, and more specifically 80°≤$_3$≤110°.

In one embodiment, the time-of-flight sensor is configured to operate at a first sample rate when the measured position is in the first zone, at a second sample rate when the measured position is in the second zone, and at a third sample rate when the measured position is in the third zone, the first sample rate being higher than the second sample rate, the second sample rate being higher than the third sample rate.

In another embodiment, the time-of-flight sensor is configured to switch from operating at a second sample rate to operating at a first sample rate when the position of the object is first measured to be in the first zone, the first sample rate being higher than the second sample rate. In one embodiment, the time-of-flight sensor is configured to remain operating at the first sample rate until a predetermined condition is met. In one embodiment, the predetermined condition is an elapsed amount of time from when the object is first measured to be in the first zone. In one embodiment, the predetermined condition is a measurement of the object outside the first zone. In one embodiment, the predetermined condition is a measurement of the object in the second zone. In one embodiment, once the predetermined condition is met, the time-of-flight sensor is configured to switch from operating at the first sample rate to operating at the second sample rate.

Additionally or alternatively, the time-of-flight sensor is configured to switch from operating at a third sample rate to operating at a second sample rate when the position of the object is first measured to be in the second zone, the second sample rate being higher than the third sample rate. In one embodiment, the time-of-flight sensor is configured to remain operating at the second sample rate until a predetermined condition is met. In one embodiment, the predetermined condition is an elapsed amount of time from when the object is first measured to be in the second zone. In one embodiment, the predetermined condition is a measurement of the object outside the second zone. In one embodiment, the predetermined condition is a measurement of the object in the third zone, and, optionally, once the predetermined condition is met, the time-of-flight sensor is configured to switch from operating at the second sample rate to operating at the third sample rate. In one embodiment, the predetermined condition is a measurement of the object in the first zone, and, optionally, once the predetermined condition is met, the time-of-flight sensor is configured to switch from operating at the second sample rate to operating at the first sample rate.

A location relative to the dispenser may be defined by a vector $(r, \theta, \varphi)$ in a spherical coordinate system, where the origin is located on a face of the dispenser, where $\theta$ is an acute angle between the location and an axis that extends perpendicularly away from the face and where $\varphi$ is an acute angle between the location and an axis that extends in the plane of the face.

The angle $\varphi$ may be an acute angle between the location and an axis that extends in the plane of the face and is aligned with a vertical axis of the dispenser.

In one embodiment, 0 cm<r<5 cm for the first zone, and, optionally, r≥5 cm for the second zone, and, further optionally, 5 cm≤r<500 cm for the second zone, and, yet further optionally, 500 cm≤r for the third zone, and, yet further optionally, 500 cm≤r≤1000 cm for the third zone.

In another embodiment, the first zone extends from r=0 cm to r=5 cm, and, optionally, the second zone extends from r=5 cm, and, further optionally, the second zone extends from r=5 cm to r=500 cm, and, yet further optionally, the third zone extends from r=500 cm, and yet further optionally, the third zone extends from r=500 cm to r=1000 cm.

In a further embodiment, 0 cm<r<10 cm for the first zone, and, optionally, r≥10 cm for the second zone, and, further optionally, 10 cm≤r<500 cm for the second zone, and, yet further optionally, 500 cm≤r for the third zone, and, yet further optionally, 500 cm≤r≤1000 cm for the third zone.

In yet another embodiment, the first zone extends from r=0 cm to r=10 cm, and, optionally, the second zone extends from r=10 cm, and, further optionally, the second zone extends from r=10 cm to r=500 cm, and, yet further optionally, the third zone extends from r=500 cm, and yet further optionally, the third zone extends from r=500 cm to r=1000 cm.

In one embodiment, 0°<φ<60° for the first zone, and, optionally, φ≥60° for the second zone, and, further optionally, 60°≤φ<120° for the second zone, and, yet further optionally, 120°≤φ for the third zone, and, yet further optionally, 120°≤φ≤180° for the third zone.

In another embodiment, the first zone extends from φ=0° to φ=600, and, optionally, the second zone extends from φ=60°, and, further optionally, the second zone extends from φ=60° to φ=120°, and, yet further optionally, the third zone extends from φ=120°, and yet further optionally, the third zone extends from φ=180° to φ=180°.

In yet another embodiment, 0° cm<φ<90° for the first zone, and, optionally, φ≥90° for the second zone, and, further optionally, 90°≤φ<180° for the second zone.

In a further embodiment, the first zone extends from φ=0° to φ=90°, and, optionally, the second zone extends from φ=90°, and, further optionally, the second zone extends from φ=90° to φ=180°.

In one embodiment, −10°<θ<10° for the first zone, and, optionally, θ≥10° and θ≤−10° for the second zone, and, further optionally, 10°≤θ<20° and −20°≤θ<−10° for the second zone, and, yet further optionally, 20°≤θ and −20°≥θ for the third zone, and, yet further optionally, 20°≤θ≤30° and −30°≤θ≤−20° for the third zone.

In another embodiment, the first zone extends from θ=−10° to θ=100, and, optionally, the second zone extends from θ=10° and from θ=−10°, and, further optionally, the second zone extends from θ=10° to θ=200 and from θ=−20° to θ=−10°, and, yet further optionally, the third zone extends from θ=20° and from θ=−20°, and yet further optionally, the third zone extends from θ=20° to θ=300 and from θ=−30° to θ=−20°.

In a further embodiment, φ defines a horizontal angle.

In yet another embodiment, φ defines a vertical angle.

In one embodiment, the time-of-flight sensor is configured to operate at a first sample rate when the measured position is in the first zone, at a second sample rate when the measured position is in the second zone, and at a third sample rate when the measured position is in the third zone, the first sample rate being higher than the second sample rate, the second sample rate being higher than the third sample rate.

In another embodiment, the time-of-flight sensor is configured to switch from operating at a second sample rate to operating at a first sample rate when the position of the object is first measured to be in the first zone, the first sample rate being higher than the second sample rate. In one embodiment, the time-of-flight sensor is configured to remain operating at the first sample rate until a predetermined condition is met. In one embodiment, the predetermined condition is an elapsed amount of time from when the object is first measured to be in the first zone. In one embodiment, the predetermined condition is a measurement of the object outside the first zone. In one embodiment, the predetermined condition is a measurement of the object in the second zone. In one embodiment, once the predetermined condition is met, the time-of-flight sensor is configured to switch from operating at the first sample rate to operating at the second sample rate.

Additionally or alternatively, the time-of-flight sensor is configured to switch from operating at a third sample rate to operating at a second sample rate when the position of the object is first measured to be in the second zone, the second sample rate being higher than the third sample rate. In one embodiment, the time-of-flight sensor is configured to remain operating at the second sample rate until a predetermined condition is met. In one embodiment, the predetermined condition is an elapsed amount of time from when the object is first measured to be in the second zone. In one embodiment, the predetermined condition is a measurement of the object outside the second zone. In one embodiment, the predetermined condition is a measurement of the object in the third zone, and, optionally, once the predetermined condition is met, the time-of-flight sensor is configured to switch from operating at the second sample rate to operating at the third sample rate. In one embodiment, the predetermined condition is a measurement of the object in the first zone, and, optionally, once the predetermined condition is met, the time-of-flight sensor is configured to switch from operating at the second sample rate to operating at the first sample rate.

Throughout this disclosure, a zone extending from A to B is a zone that: extends from A or extends from a value infinitesimally larger than A; and/or extends to B or extends to a value infinitesimally smaller than B. In other words, a zone extending from A to B is a zone that: extends up to and including A or extends up to and including a value infinitesimally larger than A; and/or extends up to and including B or extends up to and including a value infinitesimally smaller than B.

According to further embodiments of the present invention, a method is provided of operating at least one function of a dispenser for dispensing a hygiene product. The method includes measuring with a time-of-flight sensor a position of an object relative to the dispenser, and using a controller to selectively operate the at least one function of the dispenser based on the measured position of the object relative to the dispenser.

Further features and effects of the dispenser and the method of operating at least one function of a dispenser according to the present disclosure will be evident from the following description of certain embodiments. In the description of these embodiments, reference is made to the accompanying drawings. The embodiments described may be combined in any sub-combination or combination without departing from the scope of this invention.

BRIEF DESCRIPTION OF THE DRAWINGS

For a better understanding of the objectives and features of the present invention and to show how the same may be carried out, reference will now be made, by way of example only, to the accompanying drawings. The accompanying drawings, which are incorporated in and constitute a part of this specification, illustrate one or more embodiments of the invention and, together with the general description given above and the detailed description given below, explain the one or more embodiments of the invention.

FIG. 3b is a side view of the dispenser of FIG. 3a.

FIG. 4b is a side view of the dispenser of FIG. 4a.

DETAILED DESCRIPTION

Figure 1:
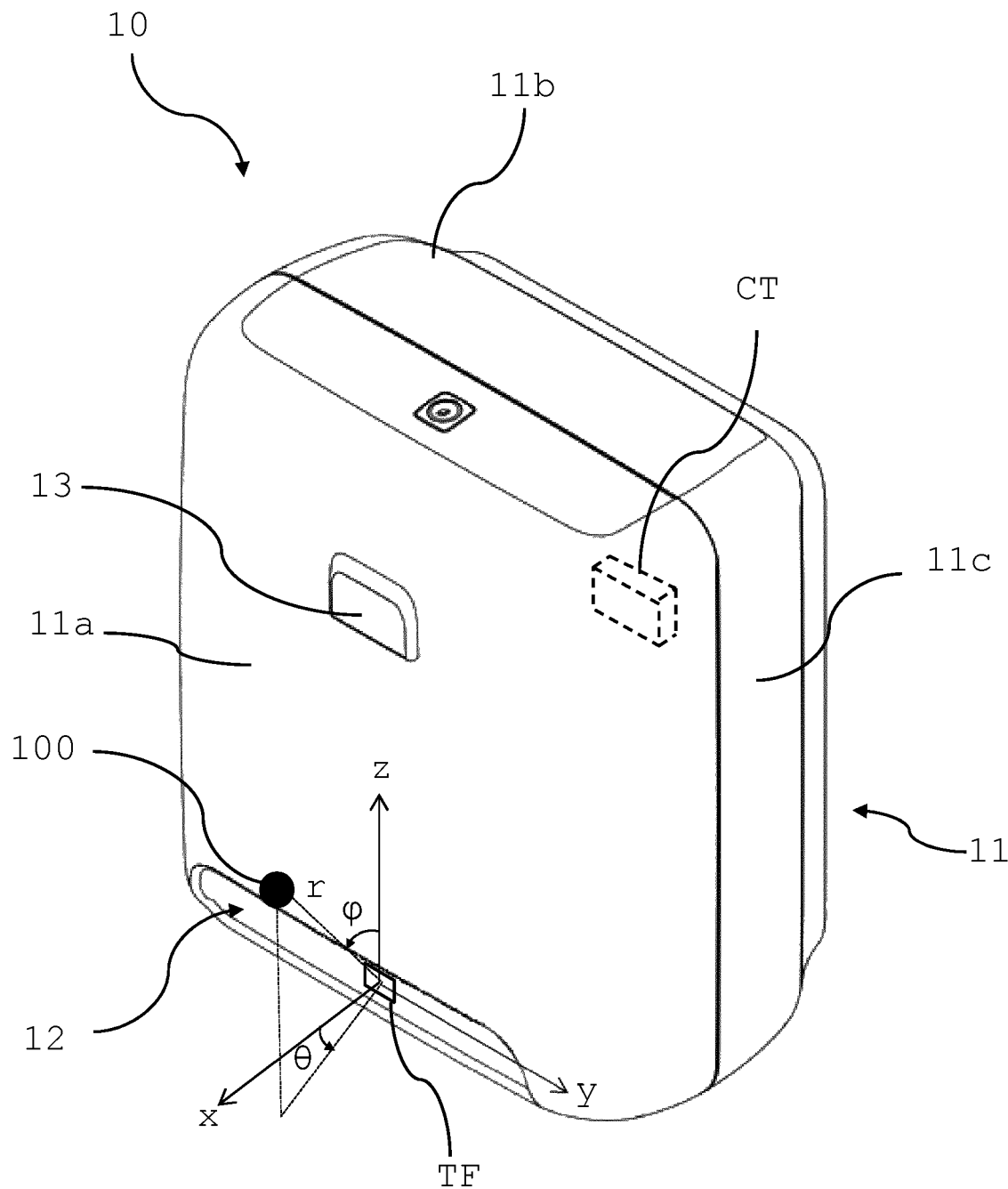
FIG. 1 is a top perspective view of a dispenser for dispensing a sheet hygiene product in accordance with one embodiment.

FIG. 1 is a perspective view of a hygiene product dispenser 10 configured to dispense a hygiene product in the form of sheets (not shown).

The dispenser 10 has a housing 11 defining an interior volume for receiving a stack of sheet products therein (not shown).

The housing 11 has a front face 11a that is configured to face toward the user of sheet product dispenser 10, a top face 11b, a bottom face (not shown), two side faces 11c (only one shown in FIG. 1), and a rear face (not shown in FIG. 1).

The front face 11a of the housing 11 defines a dispensing opening 12 for dispensing one or more of the sheet products therethrough. The dispenser 10 further includes a dispensing mechanism (not shown) that is actuatable to dispense one or more of the sheet products through the dispensing opening 12.

The dispenser 10 also includes a display 13. The display 13 may be an LCD display or LED panel on which information id displayed. The displayed information may, for example, relate to operation of the dispenser 10, such as an indication of whether or not the dispenser 10 is operational and/or the amount of sheet product remaining in the dispenser 10.

The dispenser 10 further comprises a time-of-flight sensor TF (schematically shown in FIG. 1). The time-of-flight sensor in the sample dispenser of FIG. 1 is located behind the dispensing opening 12, although other locations are similarly contemplated.

The time-of-flight sensor TF measures a position of an object 100 relative to the dispenser 10. In the illustrated embodiment, the time-of-flight sensor TF may determine the position of an object 100 in three dimensions.

As shown in FIG. 1, the position of the object 100 relative to the dispenser 10 may be represented by a three-component vector $(r, \theta, \varphi)$ in a spherical coordinate system. For example, as shown in FIG. 1, the spherical coordinate system may have its origin located at the dispensing opening 12 on the front face 11a of the dispenser 10.

As also shown in FIG. 1, a location relative to the dispenser may be defined by a vector $(x, y, z)$ in a Cartesian coordinate system with the origin disposed on the front face 11a of the dispenser 10, where the positive x axis extends perpendicularly away from the front face 11a of the dispenser 10. As shown, the y axis aligns with a horizontal axis of the dispenser and the z axis aligns with a vertical axis of the dispenser 10.

In the spherical coordinate system, and referring particularly to FIG. 1, $\theta$ is an acute angle defined on the X-Y plane, between a line projecting from the origin to the position of the object 100 and an axis that extends perpendicularly away from the front face 11a i.e., the x axis. The symbol $\varphi$ represents an acute angle defined on the X-Z plane, between a hypothetical line projecting from the origin to the position of the object 100 and an axis that extends in the plane of the front face 11a and which is aligned with the vertical axis of the dispenser 10 i.e., the z axis.

The dispenser 10 has a controller CT (schematically shown), which is configured to selectively operate at least one function of the dispenser 10 based on the measured position of the object 100 relative to the dispenser 10. Specifically, the controller CT may be configured to operate the at least one function when the measured position of the object 100 meets certain predetermined criteria. To that end, the controller CT is communicatively coupled to the time-of-flight sensor TF such that the time-of-flight sensor TF can provide data relating to the measured position of the object 100 to the controller CT. Examples of various predetermined criteria are described below in connection with FIGS. 3a to 6.

The functions of the dispenser 10 may be any one or combination of the functions described herein.

For example, a dispensing function of the dispenser 10 may be to dispense an amount (e.g., a number of sheets) of the hygiene product from the dispenser 10 such that this amount of the hygiene product is delivered to the user or is ready for the user to retrieve from the dispenser 10. In this embodiment, the dispensing function of dispenser 10 is such that the dispensing mechanism of the dispenser 10 is actuated to thereby cause a predetermined amount of the sheet product to be delivered through the opening 12 of the dispenser 10.

As another example, the dispenser 10 may have a display function. The display function of the dispenser 10 includes displaying information to the user on the display 13.

In the example embodiment of FIG. 1, the dispenser 10 further includes a battery (not shown) for supplying power to the various elements of the dispenser 10, such as the time-of-flight sensor, controller, dispensing mechanism, and/or display 13.

Figure 2:
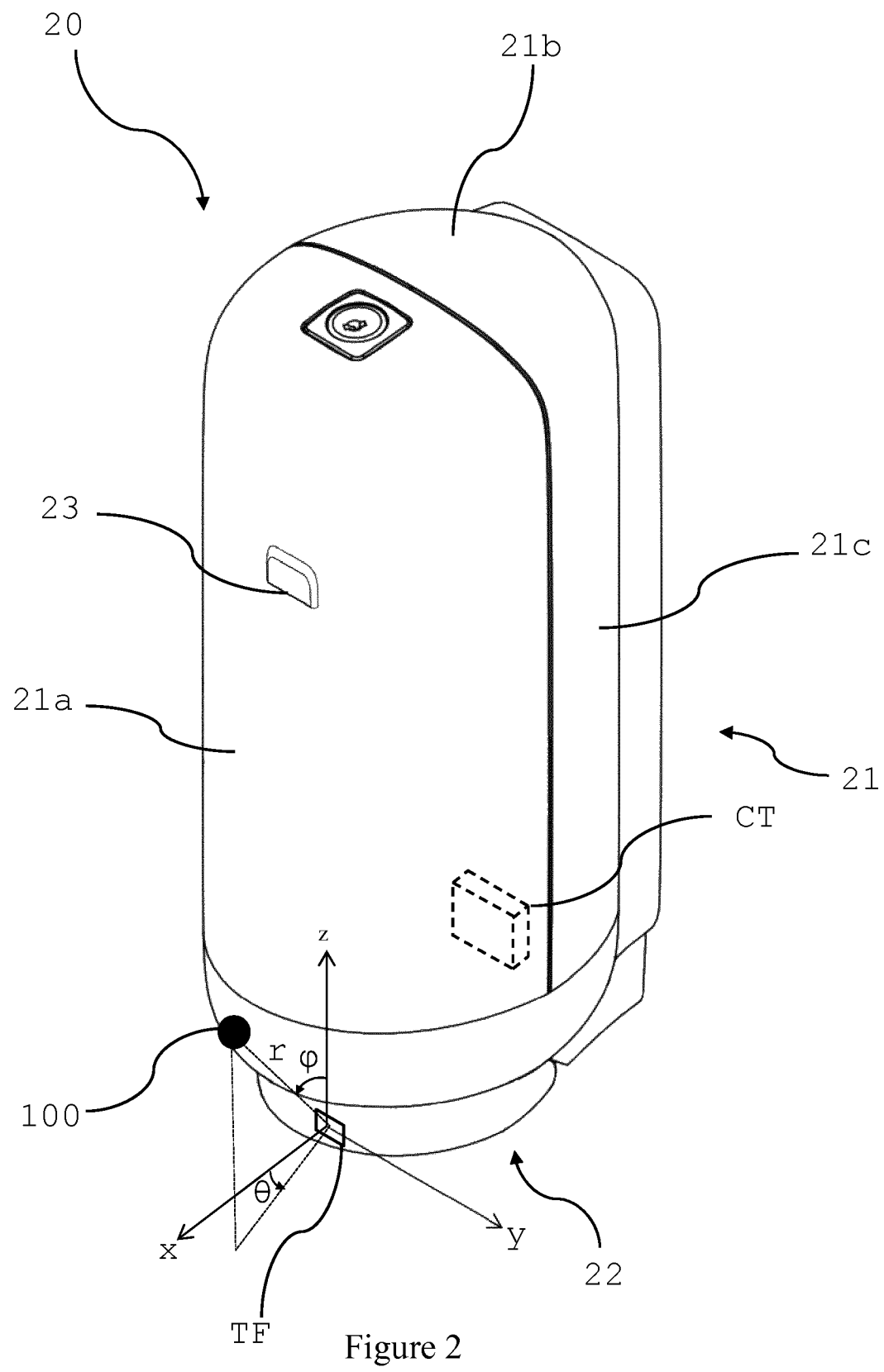
FIG. 2 is a top perspective view of a dispenser for dispensing a liquid hygiene product in accordance with another embodiment.

Reference is now made to FIG. 2, which is a perspective view of a hygiene product dispenser 20 configured for dispensing a liquid hygiene product (not shown).

The dispenser 20 includes features similar to those in dispenser 10 (FIG. 1). For ease of understanding, those features are given similar reference signs and numerals.

Dispenser 20 has a housing 21 that defines an interior volume for receiving a liquid therein (not shown).

The housing 21 has a front face 21a that is configured to face toward the user of the dispenser 20, a top face 21b, a bottom face (not shown), two side faces 21c (only one shown in FIG. 2), and a rear face (not shown in FIG. 2).

The housing 21 defines a dispensing opening 22 for dispensing an amount of the liquid therethrough. The dispenser 20 further includes a dispensing mechanism (not shown) that is actuatable to thereby dispense the liquid through the dispensing opening 22.

The dispenser 20 also includes a display 23. The display 23 may be an LCD display or LED panel on which information is displayed related to operation of the dispenser 20. The displayed information may for example be an indication as to whether or not the dispenser 20 is operational and/or the amount of liquid remaining in the dispenser 20.

The dispenser 20 further includes a time-of-flight sensor TF (schematically shown in FIG. 2) similar to that described in relation to the dispenser 10 (FIG. 1). The time-of-flight sensor TF in dispenser 20 is located behind the dispensing opening 22, although other locations are similarly contemplated.

As shown in FIG. 2, in a similar manner to dispenser 10, the position of the object 100 relative to the dispenser 20 may be represented by a three-component vector (r, θ, φ) in a spherical coordinate system. For example, as shown in FIG. 2, the spherical coordinate system may have its origin located at the dispensing opening 22 on the front face 21a of the dispenser 20.

In the spherical coordinate system, and referring to FIG. 2, θ is an acute angle—defined on the X-Y plane—between a line projecting from the origin to the position of the object 100 and an axis x that extends perpendicularly away from the front face 21a. The symbol φ refers to an acute angle defined—on the X-Z plane—between a line projecting from the origin to the position of the object 100 and an axis z that extends in the plane of the front face 11a and that is aligned with the vertical axis of the dispenser 20.

The dispenser 20 further includes a controller CT (schematically shown in FIG. 2) similar to that described in relation to the dispenser 10 of FIG. 1. Again, examples of the various predetermined criteria are described below in relation to FIGS. 3a to 6.

The functions of the dispenser 20 may be any one or combination of the functions described herein.

For example, a dispensing function of the liquid product dispenser 20 may include dispensing an amount (e.g., a predetermined weight or volume) of the liquid hygiene product from the dispenser 20, with that amount being delivered to the user or making that amount ready for retrieval by the user from the dispenser. In this example embodiment, the dispensing function includes actuation of the dispensing mechanism of the dispenser 10 such that a predetermined amount of the liquid product is delivered through the opening 22 of the dispenser 20.

As another example, the dispenser 20 also has a display function similar to that described in relation to the dispenser 10 of FIG. 1.

In the illustrated embodiment, the dispenser 20 also includes a battery (not shown) for supplying power to the various elements of the dispenser 20, such as the time-of-flight sensor, controller, dispensing mechanism, and/or display 23.

Various configurations of the controller and the time-of-flight sensor are contemplated. For ease of explanation and understanding, the generic dispensers shown in FIGS. 3a to 6 may refer to a sheet product dispenser such as dispenser 10 (FIG. 1) or to a liquid product dispenser such as dispenser 20 (FIG. 2), and each may include all of the elements described above in connection to the embodiments of FIGS. 1 and 2. Similar reference numerals denote similar elements.

Figure 3A:
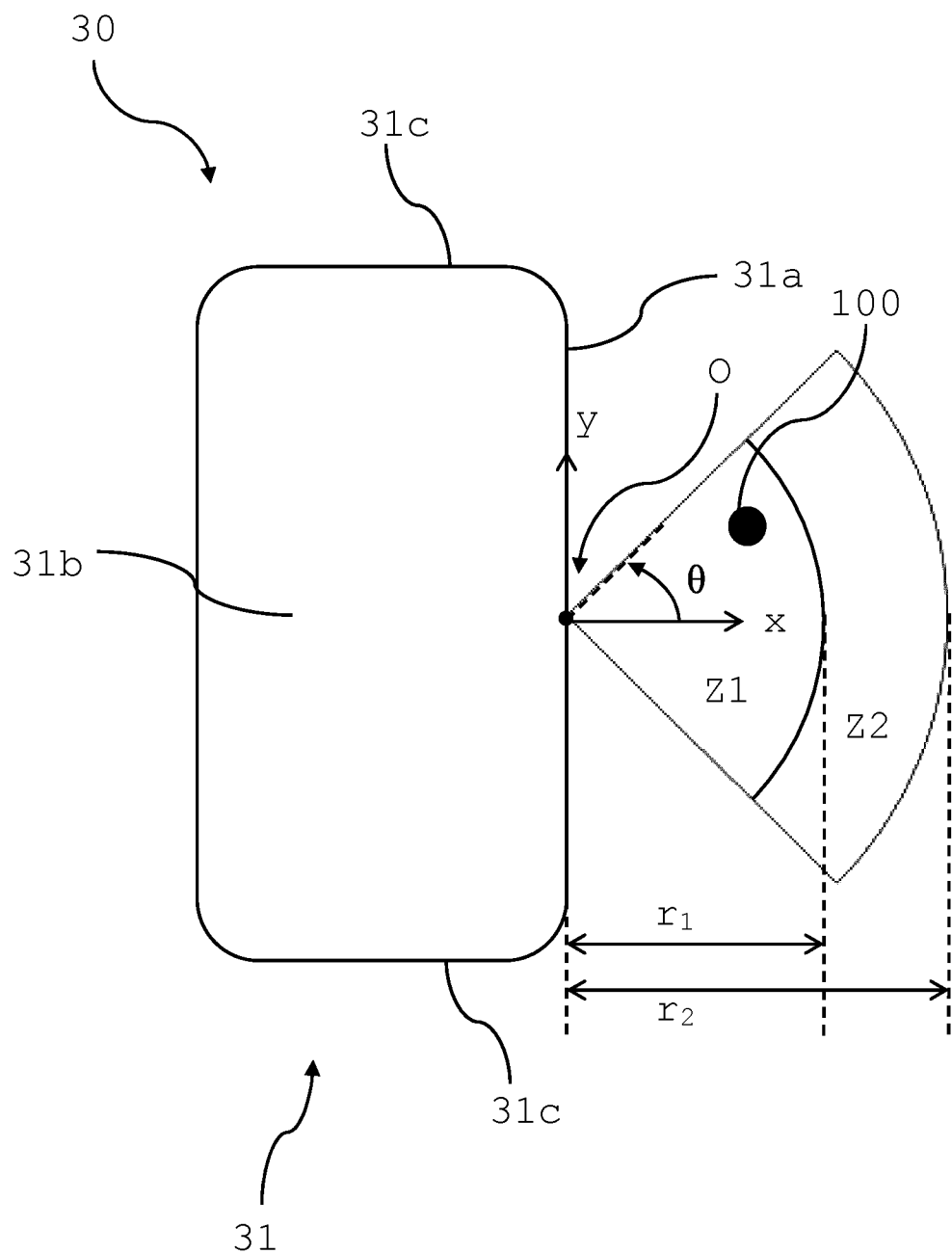
FIG. 3a is a top plan view of a dispenser for dispensing a hygiene product in accordance with yet another embodiment.
Figure 3B:
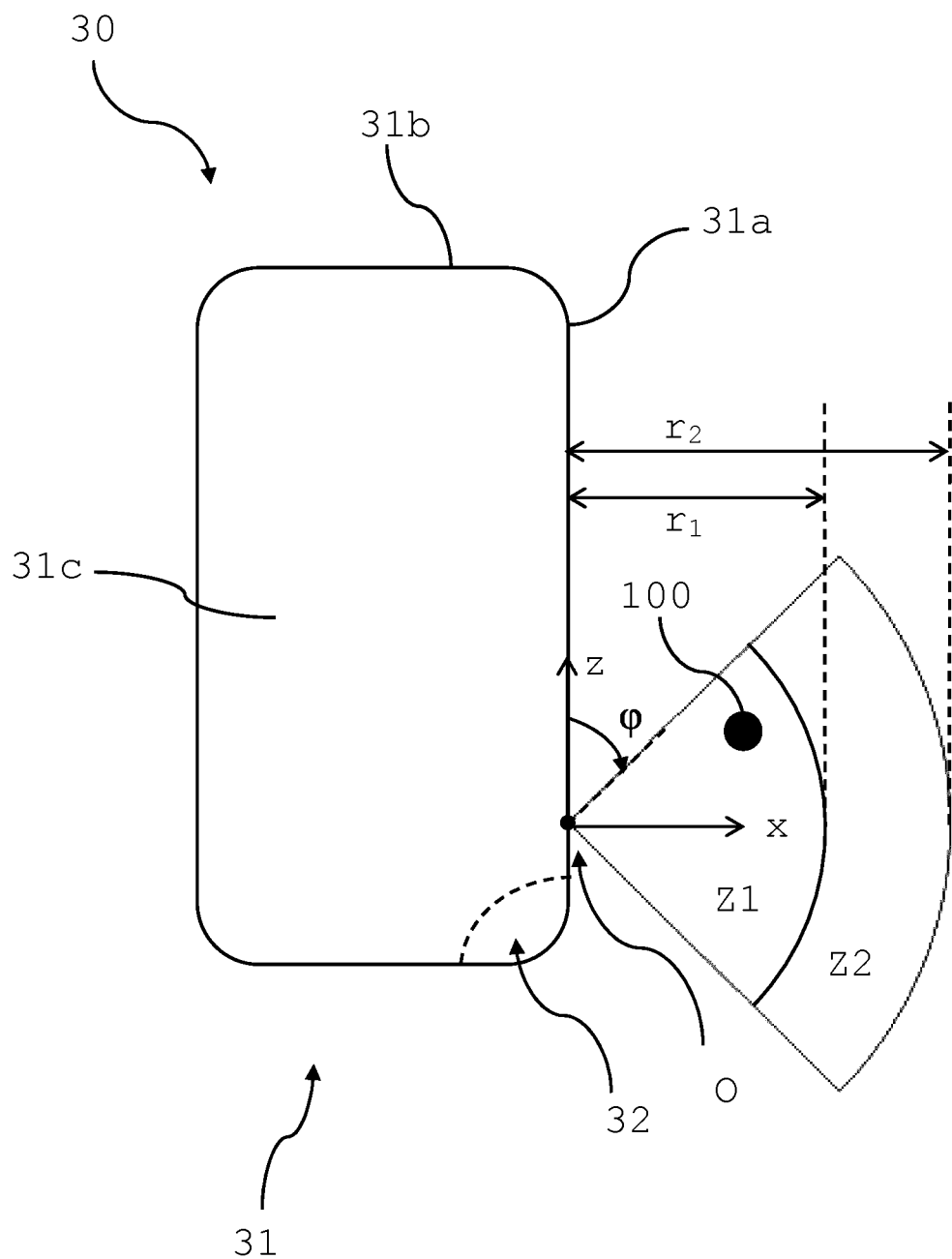

With reference to FIGS. 3a and 3b, a dispenser 30 is configured for dispensing a hygiene product.

FIG. 3a shows a front face 31a, a top face 31b, and two side faces 31c of the housing 31. FIG. 3b shows the front face 31a, the top face 31b, and one of the two side faces 31c of a housing 31 of dispenser 30. FIG. 3b also shows a dispensing opening 32 of the dispenser 30.

In the illustrated embodiment, a controller of dispenser 30 is configured to operate a first function of the at least one function of the dispenser 30 when the measured position of an object 100 is in a first zone Z1. The controller is also configured to operate a second (different) function of the at least one function of the dispenser 30 when the measured position of the object 100 is in a second zone Z2. The functions operated in the first zone Z1 and the second zone Z2 may be any one or combination of the functions described herein.

As can be seen in FIGS. 3a and 3b, the first zone Z1 is closer to the dispenser than is the second zone Z2.

In this embodiment, the first zone Z1 is a three-dimensional region having the shape of a spherical cone of radius $r_1$ centered at an origin O and having an axis extending perpendicularly away from the front face 31a (i.e., coincident with the x axis).

The second zone Z2 is a three-dimensional region having the shape defined by a spherical cone of radius $r_2$ centered at the origin O and having an axis extending perpendicularly away from the front face 31a and excluding the volume occupied by the spherical cone of radius $r_1$ centered at the origin O and having an axis extending perpendicularly away from the front face 31a. Accordingly, the second zone Z2 is a three-dimensional region defining a circular shell having a thickness of $r_2-r_1$, the axis of the circular shell being coincident with the axis of the spherical cone of the first zone Z1.

Accordingly, in the spherical coordinate system shown in FIGS. 1 and 2 (and partially shown in FIGS. 3a and 3b), the first zone Z1 extends from $r=0$ to $r=r_1$, from $\theta=-\theta_1$ to $\theta=+\theta_1$, and from $\varphi=\varphi_1$ to $\varphi=\varphi_{1'}$. For example, $r_1=5$ cm or 10 cm, $\theta_1=45°$, $\varphi_1=45°$ and $\varphi_{1'}=135°$.

The second zone Z2 extends from $r=r_1$ to $r=r_2$, from $\theta=-\theta_2$ to $\theta=+\theta_2$, and from $\varphi=\varphi_2$ to $\varphi=\varphi_{2'}$. For example, $r_1=5$ cm or 10 cm, $r_2=100$ cm, $\theta_2=450$, $\varphi_2=45°$ and $\varphi_{2'}=135°$.

Figure 4A:
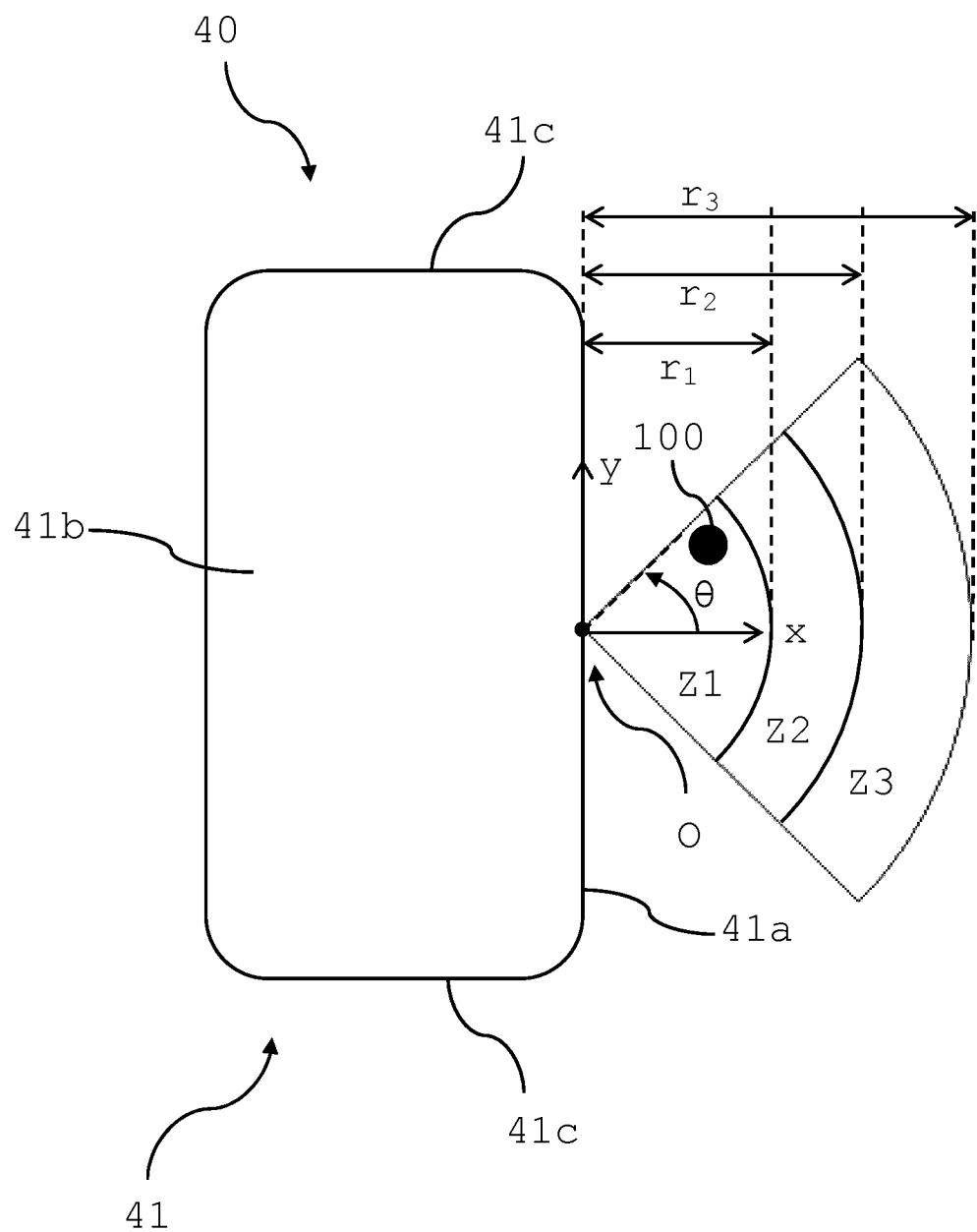
FIG. 4a is a top plan view of a dispenser for dispensing a hygiene product in accordance with another embodiment.
Figure 4B:
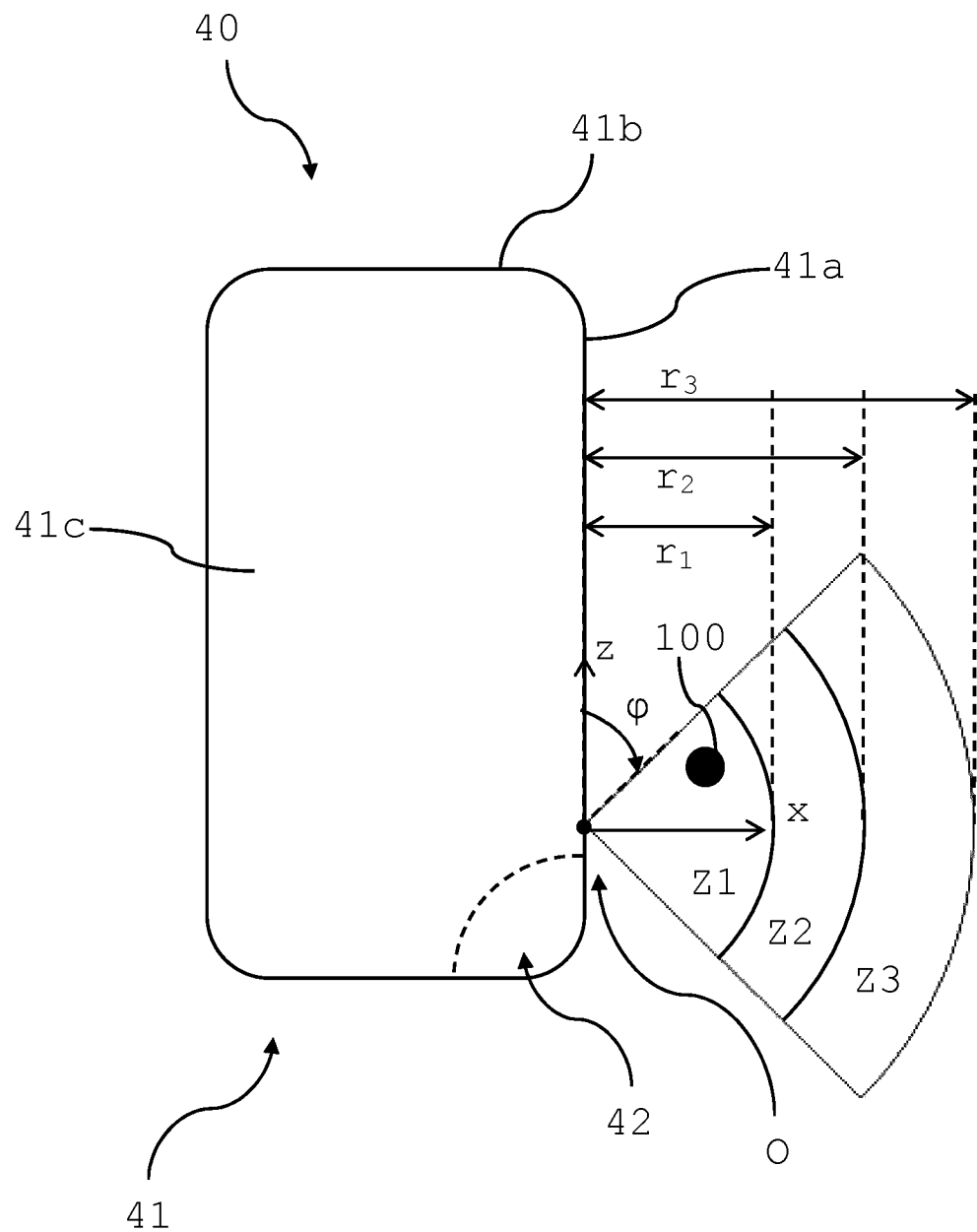

Turning now to FIGS. 4a and 4b. those figures show a dispenser 40 for dispensing a hygiene product.

FIG. 4a shows a front face 41a, a top face 41b, and two side faces 41c of a housing 41 of dispenser 40. FIG. 4b shows the front face 41a, the top face 41b, and one of the two side faces 41c of the housing 41. FIG. 4b also shows a dispensing opening 42 of the dispenser 40.

In this example embodiment, a controller of dispenser 40 is configured to operate a first function of the at least one function of the dispenser 40 when the measured position of an object 100 is in a first zone Z1. The controller is also configured to operate a second (different) function of the at least one function of the dispenser 40 when the measured position of the object 100 is in a second zone Z2. The controller is further configured to operate a third (different) function of the at least one function of the dispenser 40 when the measured position of the object 100 is in a third zone Z3. The functions operated in the first zone Z1, the second zone Z2, and the third zone Z3 may be any one or combination of the functions described herein.

As can be seen in FIGS. 4a and 4b, the first zone Z1 is closer to the dispenser 40 than is the second zone Z2 and the second zone Z2 is closer to the dispenser 40 than is the third zone Z3.

In this illustrated embodiment, the first zone Z1 is a three-dimensional region having the shape of a spherical cone of radius $r_1$ centered at an origin O and having an axis extending perpendicularly away from the front face 41a.

The second zone Z2 is a three-dimensional region having the shape defined by a spherical cone of radius $r_2$ centered at the origin O and having an axis extending perpendicularly away from the front face 41a and excluding the volume occupied by a spherical cone of radius $r_1$ centered at the origin O and having an axis extending perpendicularly away from the front face 41a. Accordingly, the second zone Z2 is a three-dimensional region having the shape of a circular shell having a thickness of $r_2-r_1$, the axis of the circular shell being coincident with the axis of the spherical cone of the first zone Z1.

The third zone Z3 is a three-dimensional region having the shape defined by a spherical cone of radius $r_3$ centered at the origin O and having an axis extending perpendicularly away from the front face 41a and excluding the volume occupied by a spherical cone of radius $r_2$ centered at the origin O and having an axis extending perpendicularly away from the front face 41a. Accordingly, the third zone Z3 is a three-dimensional region having the shape of a circular shell having a thickness of $r_3-r_2$, the axis of the circular shell being coincident with the axis of the spherical cone of the first zone Z1.

Accordingly, in the spherical coordinate system shown in FIGS. 1 and 2 (and partially shown in FIGS. 4a and 4b), the first zone Z1 extends from $r=0$ to $r=r_1$, from $\theta=-\theta_1$ to $\theta=+\theta_1$, and from $\varphi=\varphi_1$ to $\varphi=\varphi_{1'}$. For example, $r_1=5$ cm or 10 cm, $\theta_1=45°$, $\varphi_1=45°$ and $\varphi_{1'}=135°$.

The second zone Z2 extends from $r=r_1$ to $r=r_2$, from $\theta=-\theta_2$ to $\theta=+\theta_2$, and from $\varphi=\varphi_2$ to $\varphi=\varphi_{2'}$. For example, $r_1=5$ cm or 10 cm, $r_2=50$ cm, $\theta_2=45°$, $\varphi_2=45°$ and $\varphi_{2'}=135°$.

The third zone Z3 extends from $r=r_2$ to $r=r_3$, from $\theta=-\theta_3$ to $\theta=+\theta_3$, and from $\varphi=\varphi_3$ to $\varphi=\varphi_{3'}$. For example, $r_2=50$ cm, $r_3=100$ cm, $\theta_3=45°$, $\varphi_3=45°$ and $\varphi_3'=135°$.

Figure 5:
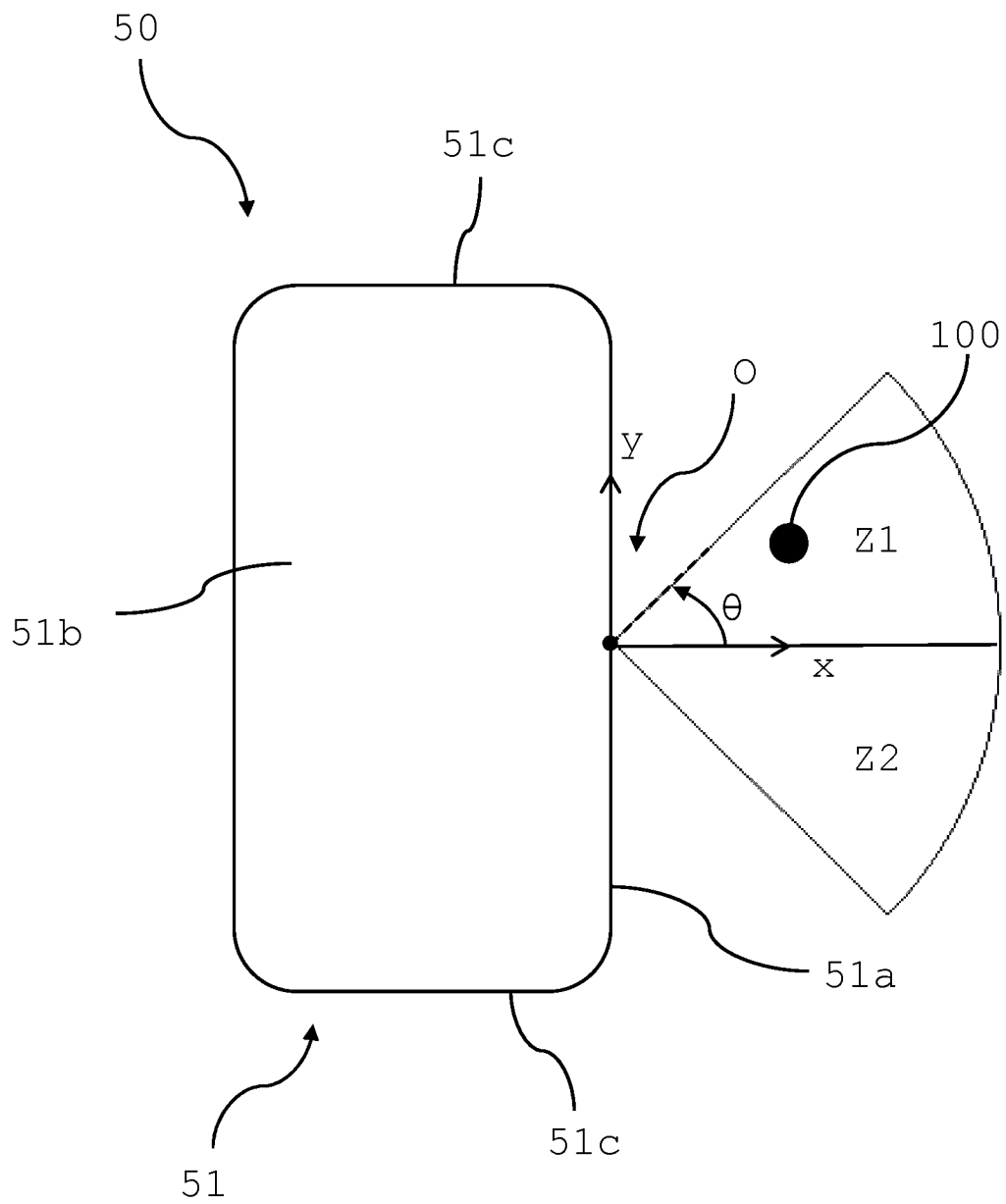
FIG. 5 is a top plan view of a dispenser for dispensing a hygiene product in accordance with yet another embodiment.

Reference is now made to FIG. 5, which shows a dispenser 50 for dispensing a hygiene product.

FIG. 5 shows a front face 51a, a top face 51b, and two side faces 51c of a housing 51 of dispenser 50.

In this example embodiment, a controller of dispenser 50 is configured to operate a first function of the at least one function of the dispenser 50 when the measured position of an object 100 is in a first zone Z1. The controller is also configured to operate a second function of the at least one function of the dispenser 50 when the measured position of the object 100 is in a second zone Z2. The functions operated in the first zone Z1 and the second zone Z2 may be any one or combination of the functions described herein.

In this embodiment, the first zone Z1 is a three-dimensional region having the shape of a half of a spherical cone of radius $r_1$ centered at an origin O and having an axis extending perpendicularly away from the front face 51a, and which lies on the positive y side of the xz-plane.

The second zone Z2 is a three-dimensional region having the shape of a half of a spherical cone of radius $r_1$ centered at the origin O and having an axis extending perpendicularly away from the front face 51a, and which lies on the negative y side of the xz-plane.

In this embodiment, there is no overlap between the first zone Z1 and the second zone Z2 and the combined three dimensional regions of the first zone Z1 and the second zone Z2 form a spherical cone of radius $r_1$ centered at the origin O and having an axis extending perpendicularly away from the front face 51a.

Accordingly, in the spherical coordinate system shown in FIGS. 1 and 2 (and partially shown in FIG. 5), the first zone Z1 extends from $r=0$ to $r=r_1$, from $\theta=0°$ to $\theta=+\theta_1$, and from $\varphi=\varphi_1$ to $\varphi=\varphi_{1'}$. For example, $r_1=100$ cm, $\theta_1=45°$, $\varphi_1=45°$ and $\varphi_{1'}=135°$.

The second zone Z2 extends from $r=0$ to $r=r_1$, from $\theta=0°$ to $\theta=-\theta_1$, and from $\varphi=\varphi_1$ to $\varphi=\varphi_{1'}$. For example, $r_1=100$ cm, $\theta_1=45°$, $\varphi_1=45°$ and $\varphi_{1'}=135°$.

The time-of-flight sensor (not shown) of the dispenser 50 may comprise two time-of-flight sensors spaced apart from each other in a horizontal direction (i.e. along a horizontal (y) axis of the dispenser 50).

The detection regions of the two time-of-flight sensors may at least partially overlap.

The time-of-flight sensor may be configured to operate at a first sample rate when the measured position is in the first zone Z1, and at a second sample rate when the measured position is in the second zone Z2, the first sample rate being higher than the second sample rate.

In another embodiment, the time-of-flight sensor may be configured to switch from operating at a second sample rate to operating at a first sample rate when the position of the object 100 is first measured to be in the first zone Z1, the first sample rate being higher than the second sample rate. In one embodiment, the time-of-flight sensor is configured to remain operating at the first sample rate until a predetermined condition is met. In one embodiment, the predetermined condition is an elapsed amount of time from when the object 100 is first measured to be in the first zone Z1. In one embodiment, the predetermined condition is a measurement of the object 100 outside the first zone Z1. In one embodiment, the predetermined condition is a measurement of the object 100 in the second zone Z2. In one embodiment, once the predetermined condition is met, the time-of-flight sensor is configured to switch from operating at the first sample rate to operating at the second sample rate.

Figure 6:
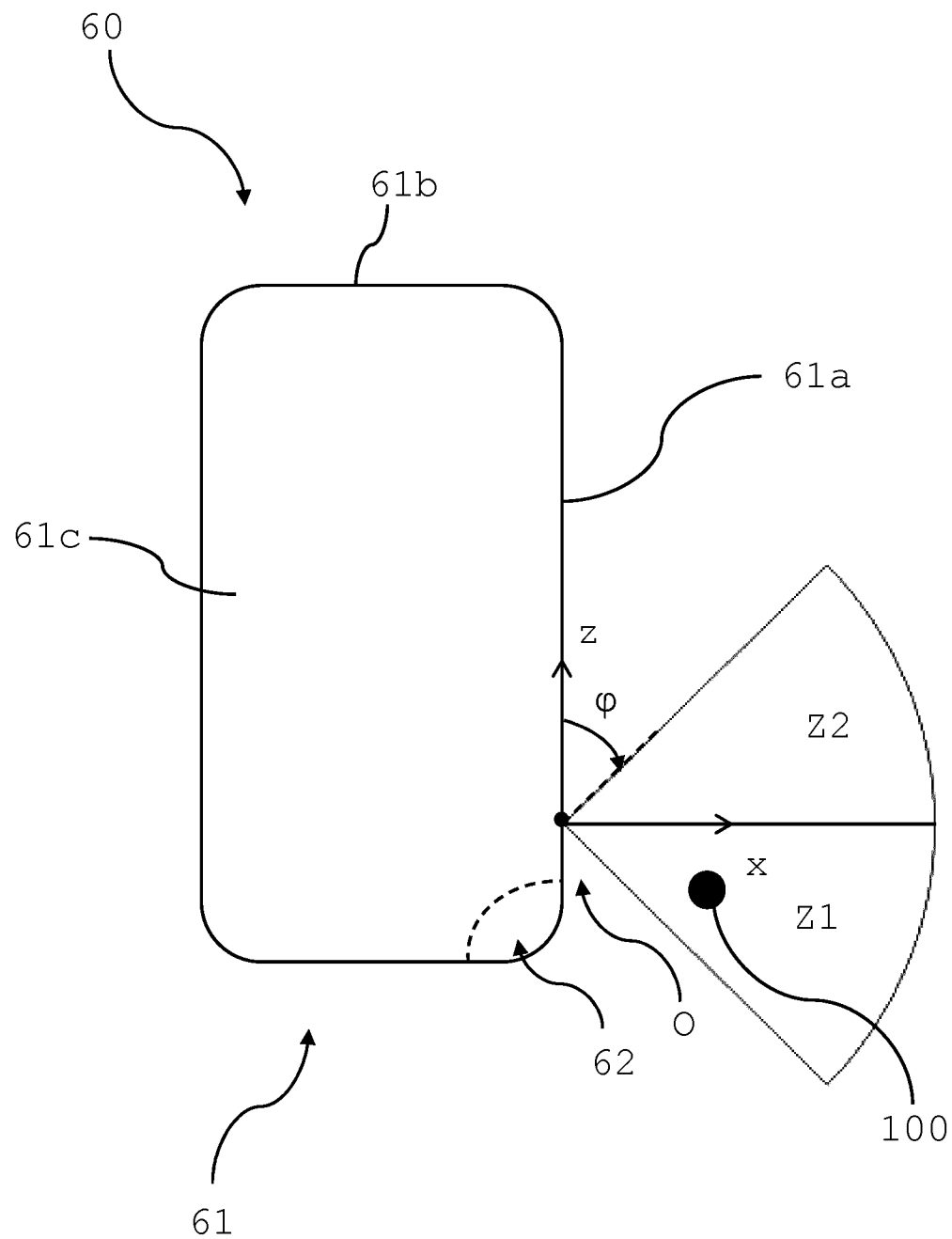
FIG. 6 is a side view of a dispenser for dispensing a hygiene product in accordance with a further embodiment.

Referring now to FIG. 6, that figure shows a dispenser 60 for dispensing a hygiene product and having.

a front face 61*a*, a top face 61*b*, and two side faces 61*c* of a housing 61 of dispenser 60. FIG. 6 also shows a dispensing opening 62 of the dispenser 60.

In this example embodiment, a controller of dispenser 60 is configured to operate a first function of the at least one function of the dispenser 60 when the measured position of an object 100 is in a first zone Z1. The controller is also configured to operate a second function of the at least one function of the dispenser 60 when the measured position of the object 100 is in a second zone Z2. The functions operated in the first zone Z1 and the second zone Z2 may be any one or combination of the functions described herein.

In this embodiment, the first zone Z1 is a three-dimensional region having the shape of a half of a spherical cone of radius $r_1$ centered at the origin O and having an axis extending perpendicularly away from the front face 61*a*, and which lies on the negative z side of the xy-plane.

The second zone Z2 is a three-dimensional region having the shape of a half of a spherical cone of radius $r_1$ centered at the origin O and having an axis extending perpendicularly away from the front face 61*a*, and which lies on the positive z side of the xy-plane.

In this embodiment, there is no overlap between the first zone Z1 and the second zone Z2 and the combined three dimensional regions of the first zone Z1 and the second zone Z2 form a spherical cone of radius $r_1$ centered at the origin O and having an axis extending perpendicularly away from the front face 61*a*.

Accordingly, in the spherical coordinate system shown in FIGS. 1 and 2 (and partially shown in FIG. 6), the first zone Z1 extends from $r=0$ to $r=r_1$, from $\theta=-\theta_1$ to $\theta=+\theta_1$, and from $\varphi=\varphi_1$ to $\varphi=\varphi_{1'}$. For example, $r_1=100$ cm, $\theta_1=45°$, $\varphi_1=45°$ and $\varphi_{1'}=90°$.

The second zone Z2 extends from $r=0$ to $r=r_1$, from $\theta=-\theta_1$ to $\theta=+\theta_1$, and from $\varphi=\varphi_2$ to $\varphi=\varphi_{2'}$. For example, $r_1=100$ cm, $\theta_1=45°$, $\varphi_2=90°$ and $\varphi_{2'}=1350°$.

The time-of-flight sensor (not shown) of the dispenser 60 may comprise two time-of-flight sensors spaced apart from each other in a vertical direction (i.e. along a vertical (z) axis of the dispenser 60).

The detection regions of the two time-of-flight sensors may at least partially overlap.

The time-of-flight sensor may be configured to operate at a first sample rate when the measured position is in the first zone Z1, and at a second sample rate when the measured position is in the second zone Z2, the first sample rate being higher than the second sample rate.

In another embodiment, the time-of-flight sensor may be configured to switch from operating at a second sample rate to operating at a first sample rate when the position of the object 100 is first measured to be in the first zone Z1, the first sample rate being higher than the second sample rate. In one embodiment, the time-of-flight sensor is configured to remain operating at the first sample rate until a predetermined condition is met. In one embodiment, the predetermined condition is an elapsed amount of time from when the object 100 is first measured to be in the first zone Z1. In one embodiment, the predetermined condition is a measurement of the object 100 outside the first zone Z1. In one embodiment, the predetermined condition is a measurement of the object 100 in the second zone Z2. In one embodiment, once the predetermined condition is met, the time-of-flight sensor is configured to switch from operating at the first sample rate to operating at the second sample rate.

The dispensers shown in FIGS. 3*a* to 6 may be, for example and without limitation, in the form of a dispenser of sheet products such as dispenser 10 of FIG. 1, or a dispenser of liquid product, such as dispenser 20 of FIG. 2. The dispenser described with reference to those figures may be provided in a suitable location for use by a user requiring a hygiene product.

As an object 100, for example a hand of a user, moves toward a dispensing opening of a dispenser, the time-of-flight sensor measures the position of the user's hand relative to the dispenser. The controller selectively operates at least one function of the dispenser based on the measured position of the user's hand relative to the dispenser.

In particular, as the user's hand moves toward the dispenser, the controller may be configured to selectively operate a second function of the at least one function of the dispenser when the measured position of the user's hand is in a second zone Z2. This second function may be a display function, for example.

As the user's hand continues to move toward the dispenser, the user's hand may enter a first zone Z1 which is closer to the dispenser than is the second zone Z2. The controller may be configured to selectively operate a first function of the at least one function of the dispenser when the measured position of the user's hand is in the first zone Z1. The first function may be a dispensing function, for example.

The dispensing function of the dispenser actuates the dispensing mechanism of the dispenser such that a predetermined amount of the hygiene product is delivered to the dispensing opening of the dispenser ready for the user to retrieve from the dispenser. The extent of the first zone Z1 may be such that the user's hand is in close proximity to the dispensing opening when the dispensing function is operated by the controller.

The user may then manually retrieve or receive the hygiene product from the dispensing opening of the dispenser.

Although the above explanation is considered to fully clarify how the present invention may be put into effect by those skilled in the art, it is to be regarded as purely illustrative.

In particular, there are a number of variations which are possible, as may be appreciated by those skilled in the art.

For example, in the embodiments shown in FIGS. 3*a* to 6, the controller is configured to operate a first function of the at least one function when the measured position of the object 100 is in a first zone Z1, and the controller is configured to operate a second function of the at least one function when the measured position of the object 100 is in a second zone Z2 and, optionally, the controller is configured to operate a third function of the at least one function when the measured position of the object 100 is in a third zone Z3.

In alternative embodiments, the controller may not activate the functions based on the position of the object being within a specified zone. Specifically, the controller may additionally or alternatively be configured to calculate a velocity of the object relative to the dispenser based on measured positions of the object, and to operate a first function of the at least one function if the velocity is within a first predetermined range of velocities. Optionally, the controller may be further configured to operate a second function of the at least one function if the velocity is within a second predetermined range of velocities.

In a further alternative embodiment, the controller may be configured to selectively operate at least one function of the dispenser in accordance with any suitable algorithm or determination process, provided that it is based on the measured position of the object relative to the dispenser.

In the embodiments shown in FIGS. 1 to 6, the controller may be configured to selectively operate at least one function of the dispenser based only on the measured position of the object 100 relative to the dispenser.

In an alternative embodiment, the controller may be configured to selectively operate at least one function of the dispenser if the direction of the velocity of the object is toward the dispenser. Furthermore, the controller may be configured to selectively operate at least one function of the dispenser based on both the measured position of the object relative to the dispenser and any other suitable factor.

By way of further example, in the embodiments shown in FIGS. 1 and 2, the dispenser 10, 20 is a dispenser 10, 20 for dispensing either a hygiene product in the form of sheets or a liquid hygiene product.

In an alternative embodiment, the dispenser may be a dispenser for dispensing napkins in the form of rolls, feminine hygiene articles or any other hygiene product that is suitable for provision to a user by a dispenser.

In a further example, in the embodiments shown in FIGS. 1 to 6, the time-of-flight sensor may be configured to operate at a single sample rate.

In the above embodiments, the time-of flight sensor operates at one sample rate. However, in an alternative embodiment, the time-of-flight sensor may be configured to operate at a first sample rate when the measured position is in a first zone and at a second sample rate when the measured position is in a second zone, the first sample rate being higher than the second sample rate. The time-of-flight sensor may be configured to operate at a third sample rate when the measured position is in a third zone, the second sample rate being higher than the third sample rate.

Alternatively, the selected sample rate may be based on the measured position of the object relative to the dispenser or any other suitable factor.

In the embodiments shown in FIGS. 1 to 6, the controller is configured to selectively operate a dispensing function or a display function.

In an alternative embodiment, the controller may be configured to operate any suitable function or any suitable combination of functions. The function may be a power-up function, a communication function, a sound function or a settings function.

Alternatively, the controller may be configured to operate a plurality of dispensing functions based on the measured position of the object relative to the dispenser, with each dispensing function including the dispensing of a different amount of hygiene product.

In a further alternative embodiment, the controller may be configured to operate a plurality of display functions based on the measured position of the object relative to the dispenser, with each display function including the display of a different piece of information.

By way of further example, in the embodiments shown in FIGS. 3a to 6, the controller is configured to selectively operate at least one function of the dispenser when the measured position of the object 100 is in one of either two zones Z1, Z2 or three zones Z1, Z2, Z3.

In an alternative embodiment, the controller may be configured to selectively operate at least one function of the dispenser when the measured position of the object is in one of four or more zones.

In light of this, there will be many alternatives that implement the teaching of the present disclosure. It is expected that one skilled in the art will be able to modify and adapt the above disclosure to suit particular circumstances and requirements within the scope of the present disclosure, while retaining some or all technical effects of same, either disclosed or derivable from the above, in light of the common general knowledge in this art. All such equivalents, modifications or adaptations fall within the scope of the invention as defined by the appended claims.

The embodiments described above are only descriptions of preferred embodiments of the present invention, and do not intended to limit the scope of the present invention. Various variations and modifications can be made to the technical solution of the present invention by those of ordinary skills in the art, without departing from the design and spirit of the present invention. The variations and modifications should all fall within the claimed scope defined by the claims of the present invention.

What is claimed is:

1. A dispenser for dispensing a hygiene product, comprising:
   a housing including a first a side face and a second side face located opposite from the first side face along a first axis to define a housing length, a rear face interposed between the first and second side faces and extending along a second axis orthogonal to the first axis to define housing height, and a front face located between the first and second side faces and arranged a distance away from the rear face along a third axis orthogonal to the first and second axes to define a housing thickness;
   a display on the front face;
   a time-of-flight sensor for measuring a position of an object relative to the dispenser;
   a controller configured to selectively operate at least one function of the dispenser based on the measured position of the object relative to the dispenser,
   wherein the controller is configured to operate a first function of the at least one function when the measured position is in a first zone extending along the third axis from a first point (R) located adjacent the front face to a second point (R1) located a first distance (R-R1) away from the first point (R), and wherein the controller is configured to operate a second function of the at least one function when the measured position is in a second zone extending along the third axis from the second point (R1) to a third point (R2) located a second distance (R1-R2) away from the first zone,
   wherein the first function is a dispensing function, and the second function is one or both of a power-up function to power up the dispenser and a display function corresponding to the display, and
   wherein the first zone is closer to the dispenser than the second zone.

2. The dispenser of claim 1, wherein the time-of-flight sensor is configured to operate at a first sample rate when the measured position is in a first zone and at a second sample rate when the measured position is in a second zone, the first sample rate being higher than the second sample rate.

3. The dispenser of claim 2, wherein the first zone is closer to the dispenser than the second zone.

4. The dispenser of claim 2, wherein the controller is configured to calculate a velocity of the object relative to the dispenser based on measured positions of the object, and wherein the controller is configured to operate a first function of the at least one function if the velocity is within a first predetermined range of velocities.

5. The dispenser of claim 1, wherein the controller is configured to operate a first function of the at least one function when the measured position is in a first zone, and wherein the controller is configured to operate a second function of the at least one function when the measured position is in a second zone.

6. The dispenser of claim 5, wherein the first function is a dispensing function.

7. The dispenser of claim 5, wherein the second function is a power-up function or a display function.

8. The dispenser of claim 1, wherein the controller is configured to calculate a velocity of the object relative to the dispenser based on measured positions of the object, and wherein the controller is configured to operate a first function of the at least one function if the velocity is within a first predetermined range of velocities.

9. The dispenser of claim 8, wherein the first function is a dispensing function which dispenses a first amount of hygiene product.

10. The dispenser of claim 9, wherein the controller is configured to operate a second function of the at least one function if the velocity is within a second predetermined range of velocities, wherein the second function is a dispensing function which dispenses a second amount of hygiene product.

11. The dispenser of claim 10, wherein a magnitude of at least some of the velocities of the first predetermined range is smaller than a magnitude of at least some of the velocities of the second predetermined range, and wherein the first amount is smaller than the second amount.

12. The dispenser of claim 8, wherein the first function is a display function which displays a first piece of information.

13. The dispenser of claim 12, wherein the controller is configured to operate a second function of the at least one function if the velocity is within a second predetermined range of velocities, wherein the second function is a display function which displays a second piece of information.

14. The dispenser of claim 8, wherein the controller is configured to operate a function of the dispenser only if a direction of the velocity is towards the dispenser.

15. The dispenser of claim 1, wherein one of the at least one function is a communication function which communicates with an external entity.

* * * * *